United States Patent [19]

Beyer et al.

[11] Patent Number: 4,634,383
[45] Date of Patent: Jan. 6, 1987

[54] PROCESS AND APPARATUS FOR THE PRODUCTION OF FILLINGS IN TEETH

[75] Inventors: Hans-Hermann Beyer, Kahl; Walter Diehl, Hanau; Karlheinz Eckert, Gründau; Kurt Eiermann, Pfungstadt; Hans-Martin Ringelstein, Frankfurt, all of Fed. Rep. of Germany

[73] Assignee: Degussa Aktiengesellschaft, Frankfurt am Main, Fed. Rep. of Germany

[21] Appl. No.: 695,631

[22] Filed: Jan. 28, 1985

[30] Foreign Application Priority Data

Feb. 3, 1984 [DE] Fed. Rep. of Germany ....... 3403779

[51] Int. Cl.$^4$ .............................................. A61C 5/04
[52] U.S. Cl. ..................... 433/226; 433/119; 433/164; 433/228.1
[58] Field of Search ............... 433/226, 228, 227, 119, 433/164

[56] References Cited

U.S. PATENT DOCUMENTS

| | | | |
|---|---|---|---|
| 1,209,906 | 12/1916 | Thurston | 433/226 |
| 1,966,446 | 7/1934 | Hayes | 433/119 |
| 2,040,179 | 5/1936 | Livingstone | 433/226 |
| 2,991,176 | 7/1961 | Clancy | 433/226 |
| 3,279,067 | 10/1966 | Hoffman | 433/226 |
| 3,914,868 | 10/1975 | Schwartz et al. | 433/226 |
| 4,064,629 | 12/1977 | Stoner et al. | 433/226 |

Primary Examiner—John J. Wilson
Attorney, Agent, or Firm—Cushman, Darby & Cushman

[57] ABSTRACT

Gold powder is inserted in a cavity for the production of fillings in teeth by means of filled gold and this is subsequently hardened mechanically. The moisture sensitivity of this process can be avoided by using a paste made of platelet shaped gold powder with a plastic, organic binder which liquifies at 20° to 45° C. and the mechanical hardening is carried out with ultrasonic.

4 Claims, 1 Drawing Figure

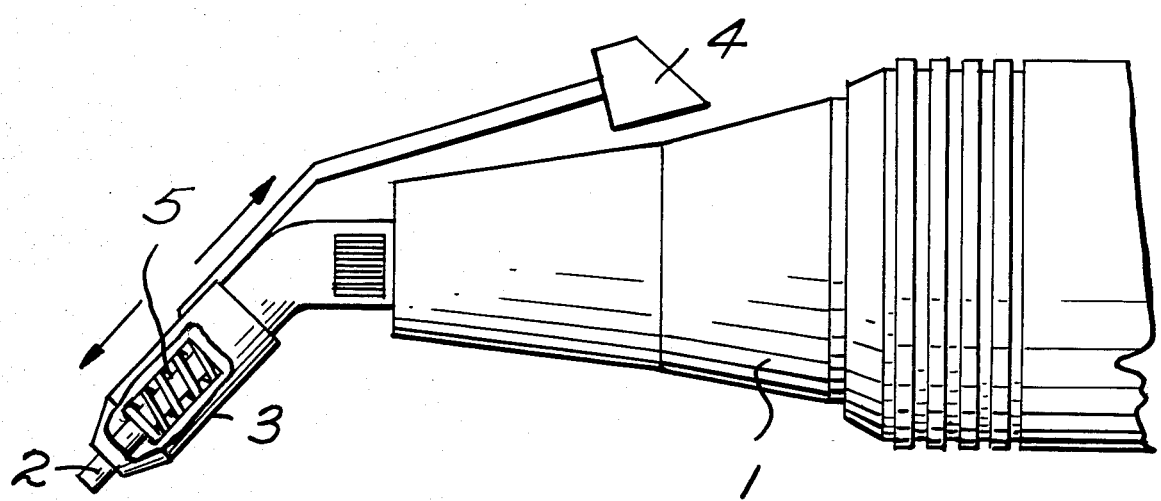

PROCESS AND APPARATUS FOR THE PRODUCTION OF FILLINGS IN TEETH

BACKGROUND OF THE INVENTION

The invention is directed to a process for the production of fillings in teeth by inserting gold powder into the cavity which is subsequently mechanically hardened and an apparatus for carrying out this process.

A number of metallic fillers are known in preserving dentistry such as for example, amalgams, cast alloys in the form of inlays, or gold fillings. The filling of the tooth cavity with gold fillings is one of the oldest methods of filling teeth. Chemically pure gold in the form of gold foil, gold sponge, or gold powder is used for these gold fillings.

the gold fillings produced from pure gold are judged excellent with regard to durability, esthetics, and resistance to corrosion. However, severe disadvantages of gold fillings are the industrial and time consuming preparation of cavity and the likewise great skill requiring depositing of the filling. Thus above all, a very careful working of the cavity with undercuts and a roughening of the cavity walls which is not automatically feasible are required. Both are absolute prerequisites for making the gold adhere sufficiently to the cavity. Furthermore, the cavity must be absolutely moisture free during the gold filling process. This involves not only the flow of saliva but also the breathing air of the patient. This requires the use of so-called cofferdam foils which is likewise time consuming, and ocassionally very unpleasant for the patient.

Furthermore, the gold filling material must be annealed in a very clean alcohol flame immediately prior to insertion into the cavity, in order that all impurities are removed from the surface and a cohesive binding is attained between the individual gold particles. The cold weldability of gold is very greatly reduced by a contamination of the surface, especially by liquid films.

A gold filling process is known from German OS No. 3042008 in which a porous sintered body or a wire ball, preferably made of gold is inserted into the cavity with a plastic or liquid organic binder and by manual filling apparatuses fitted to the cavity and hardened. Trouble free surfaces cannot be produced via these processes, which in addition are not pure metal but still contain the organic binder, usually methacrylate.

Therefore, it was the problem of the present invention to develop a process for the production of fillings in teeth by inserting gold powder into the cavity and by subsequently mechanically hardening it, a process which is not sensitive to moisture, and which permits a quick working and supplies a trouble free metallic surface.

SUMMARY OF THE INVENTION

This problem was solved according to the invention by using a plate shaped gold powder which is worked into a paste with a plastic organic binder, liquifying at 20° to 45° C., and in that the mechanical hardening takes place by ultrasonic action.

Preferably, polyethylene glycol having a molecular weight of 600 to 1500 in an amount of 0.5 to 5 weight percent is used as a binder. It has proven very advantageous to add about 2.6 wt. % of polyethylene glycol.

The gold platelets advantageously have a size of 5 to 100 $\mu$m.

A paste is produced from the platelet shaped gold powder and the organic binder which must be unobjectionable physiologically, and this paste is inserted into the cavity with a tool where it is adapted and hardened to the cavity under pressure and ultrasonic action.

Excess binder material thereby is eliminated and can be removed. Water or saliva soluble binders are used advantageously.

Preferably an apparatus which consists of a producer of ultrasonics having a rod shaped sonotrode is used for the process according to the invention. The sonotrode thereby is surrounded by a casing which can be slid forward and back. If the jacket is pushed over the point of the sonotrode, the paste can be taken up with the overlying part of the jacket and after being pushed back this can be compressed in the cavity with the sonotrode. Surprisingly the ultrasonic action completely eliminates the influence of moisture on the weldability of the gold paste, so that the fillings can be applied even under water or saliva.

BRIEF DESCRIPTION OF THE DRAWINGS

The single FIGURE of the drawing shows schematically in cross section an illustrative form of the apparatus.

DETAILED DESCRIPTION

Referring to the drawings a rod shaped Sonotrode 2 is fastened to the ultrasonic generator. The Sonotrode is enclosed in a slidable jacket 3. There is fastened on the jacket 3 a lever 4 which with help of the return spring 5 permits the jacket 3 to be slid forward and back.

The process can comprise, consist essentially of, or consist of the stated steps.

The following example explains the invention in greater detail.

EXAMPLE

Platelet shaped gold powder (15×0.3 um$^2$) is made into a paste with 2.6 wt. % polyethylene glycol (molecular weight about 800, M.P. about 28° C.). This paste is inserted in portions into the cavity of a tooth with an apparatus according to the drawing and hardened with a pressing force of 5N (at least 3N should be used) and an ultrasonic frequency of 28 kilohertz. After 10 minutes the cavity is filled. After polishing there is obtained a surface hardness of 40 vickers.

What is claimed is:

1. In a process for the production of a filling in a tooth cavity by inserting gold powder into the cavity and subsequently mechanically hardening said powder, the improvement comprising employing a platelet shaped gold powder, working said gold powder into a paste with a plastic organic binder that liquifies at 20° to 45° C., inserting said paste into said cavity and mechanical hardening said paste by ultrasonic action.

2. A process according to claim 1 wherein there is employed 0.5 to 5 wt. % of polyethylene glycol molecular weight 600 to 1500 as the binder.

3. A process according to claim 2 wherein the gold platelets have a size of 5 to 100 $\mu$m and a thickness of 0.1 to 5 $\mu$m.

4. A process according to claim 1 wherein the gold platelets have a size of 5 to 100 $\mu$m and a thickness of 0.1 to 5 $\mu$m.

* * * * *